United States Patent [19]

Beasley

[11] Patent Number: 4,661,187
[45] Date of Patent: Apr. 28, 1987

[54] METHOD OF MAKING LIFE-LIKE PROSTHETIC DEVICES

[76] Inventor: Robert W. Beasley, 251 E. 32nd St., New York, N.Y. 10016

[21] Appl. No.: 719,355

[22] Filed: Apr. 3, 1985

[51] Int. Cl.$^4$ ............................................. B29B 13/10
[52] U.S. Cl. .................................. 156/242; 264/102; 264/154; 264/222; 264/227; 623/57
[58] Field of Search ............... 264/221, 222, 223, 227, 264/102, 154, 224, 39, 40.1, 29.7; 623/57, 63, 64, 66; 156/242

[56] References Cited

U.S. PATENT DOCUMENTS

| | | | |
|---|---|---|---|
| 2,453,604 | 11/1948 | Tenenbaum et al. | 264/224 X |
| 2,508,156 | 5/1950 | Gillman | 264/224 |
| 3,244,787 | 4/1966 | Levitt | 264/223 |

Primary Examiner—Jan Silbaugh
Assistant Examiner—Harold Y. Pyon
Attorney, Agent, or Firm—Lieberman, Rudolph & Nowak

[57] ABSTRACT

Prosthetic devices of utilitarian, yet natural and unprecedented life-like appearance, are formed of durable elastomers. A seamless flexible negative mold of a biological body member selected to form the basic model is made by painting on to it nylon mesh-reinforced silicone with direct monitoring and correction of the positioning of the parts. A positive wax model is cast in the mold and subsequently modified by sculpturing to the requirements of the individual for whom the prosthesis is being developed. From the master wax model a negative metal mold is made by electroplating. New and unique provisions for ventilation to effectively remove from the molds solvents of the elastomer dispersions greatly improve the quality and rapidity of production. Invented methods of creating ventilation ports without damage to the critical interior surface of the molds and of degassing the dispersions to eliminate bubble defects are employed. A method of coloration is utilized which closely mimics the pigmentation pattern of normal skin achieving an unprecedented natural appearance. Fingernails precisely duplicated in acrylics are inlayed with a new and secure method of fixation in the case of hand or finger prostheses. Major problems of appropriately filling the prosthetic devices with facility and without distortion have been solved by developing a method of prefabricating the internal filling units. Active or passive mechanical utilitarian devices can be readily incorporated into the versatile prefabricated units.

22 Claims, 6 Drawing Figures

FIG. IA
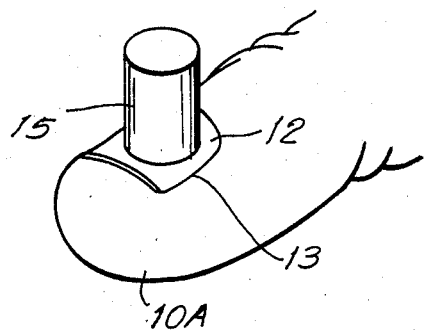
FIG. IB
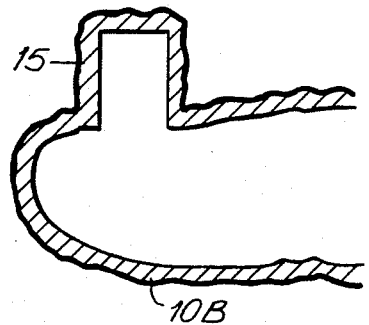
FIG. IC
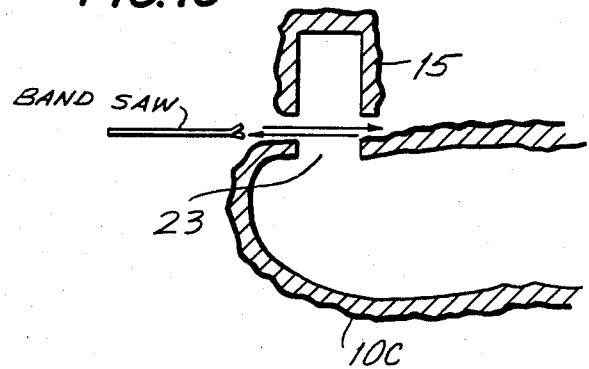

… …

METHOD OF MAKING LIFE-LIKE PROSTHETIC DEVICES

BACKGROUND OF THE INVENTION

This invention relates generally to prosthetic devices, and more particularly, to a life-like prosthetic device, such as a hand, finger, or a portion thereof, which can be worn by a person to simulate, and insofar as possible, to substitute physically for a missing or damaged body part.

The need for life-like prosthetics has long been recognized and various attempts have been made to produce prosthetic devices which restore some utility of the missing part to the amputee. Possibly of equal significance today, is the need to restore near-normal appearance to satisfy the psychological requirements of persons missing visible body parts by restoring insofar as possible, the devastated body image, particularly with respect to body members at or below the forearm. Many amputees have an extreme need for an assisting prosthetic device which has a natural and life-like appearance to help restore damaged body image while minimizing attention drawn to their loss which is viewed as a serious stigma. It is unrealistic in our mobile and competitive society not to recognize that the stigma of dismemberment is a serious socio-economic handicap for the amputee.

One prior art attempt at producing a life-like hand prosthesis is described in U.S. Pat. No. 2,453,604. In accordance with this known system, a product is produced which is intended to resemble a human hand, and which may be used either in the form of a glove for covering mechanical apparatus, or which may be filled to form an artificial hand. In accordance with this known system, a coating of latex is applied in a known manner, such as by spraying, to a human hand which serves as the model from which the prosthetic device is formed. The sprayed-on material is then peeled off of the human hand, in the same manner that a rubber glove is removed, and various painting procedures are performed while the glove is in an inside-out state.

In accordance with a further known method of making a cosmetic glove, the mold is produced by electro-deposition, and a cosmetic glove formed on a vinyl chloride polymer or co-polymer is then cast therein. The resulting thin glove is then pigmented using soluble colors to diffuse into the resin which forms the glove, or alternatively, insoluble colors are used. The glove is turned inside-out during the painting process to facilitate the application of pigmentation and the glove is subsequently reversed so that the colors are located on the inside surface of the glove during its usage.

None of the artificial or prosthetic items produced in accordance with the known methods have perfection of life-like or natural characteristics, nor do any of the devices of known methods using polyvinyl chloride have a practical service life with regular utilization.

It is, therefore, an object of this invention to provide a reliable, safe, fast, versatile and economical method of producing prosthetic devices such as an artificial hand or finger, which are near-natural and alive in appearance with, or without, the incorporation of various mechanical aids to improve their utility according to the individual requirements.

It is also an object of this invention to provide a reliable method for producing coloration of prosthetic devices mimicking the natural method of skin coloration to result in an appearance of natural skin with translucency, shading and variations in coloration as occurs in the wide variety of individual human skin colors.

It is also an object of this invention to provide a method for forming a prosthetic device having the resilient characteristics of the tissue of the body member after which it is being modeled.

It is still a further object of this invention to provide a prosthetic device having a fingernail of normal appearance and feeling to touch, which is inlayed for normal definition with attachment being accomplished in a secure and durable manner.

Another object of this invention is to provide a method wherein artificial body members can be constructed of materials that are non-irritating to the skin, durable, stain resistant and repairable while having a relatively long service life.

It is still another object of this invention to facilitate fabrication of a prosthetic device by providing a rapid, practical method for reliably removing solvents from chemical dispersions of the elastomers or other materials from the prostheses.

It is a further object of this invention to provide a reliable method of procurring ventilation ports in the metallic molds for a prosthetic device, by providing ports of optimal size and position without risk of damage to the delicate interior surface details of the seamless metal molds.

It is yet a further object of this invention to provide a method of forming prosthetic devices wherein a thin and delicate outer layer of the prosthetic device is easily released from a seamless negative metal mold from which the finest of details are reproduced faithfully.

It is another object of this invention to provide a reliable and expedient prefabricating method of filling the interior of the thin outer portion of the prosthesis, that corresponding to human skin, with a material of variable density, shape and other characteristics as determined by the individual needs and to install such perfabricated internal unit without changes in the shape, color or other details of the thin and pliable outer shell and with provisions of the method to also permit incorporation of metal stabilizers for the parts or a variety of mechanical assisting devices.

It is still another object of this invention to provide a reliable method of producing the prosthetic outer shell consistently free of entrapped bubbles or other defects and to do so in a short period of time.

DESCRIPTION OF PREFERRED EMBODIMENTS

The foregoing and other objects are achieved with this invention by a method of forming a prosthetic body member modeled substantially from a biological body member. In accordance with the invention, a thin coat of silicone (a polymer of dimenthyl siloxane) or other elastomer is painted onto the biological body member. Precise positioning of the parts can be observed and corrected before the elastomer cures in contrast to the "blind" and known immersion technique of embedding the parts in a container of impression material. In one embodiment, the elastomer is a silicone of a type which vulcanizes at room temperature (RTV). Since RTV silicone is relatively weak and tears easily, a layer of elastic nylon mesh is installed on the outer surface of the painted thin layer of silicone to prevent tear perpetuation. A subsequent and somewhat thicker layer of RTV silicone, is applied over the elastic nylon mesh and previous coat of material to result in a strong and seamless flexible impression negative mold of the parts in the desired positions. This makes possible, without tearing of the mold, its removal from a large part such as a hand through a narrow opening such as the wrist.

The resulting flexible impression mold is removed after curing of the silicone from the biological member; tearing being prevented even with odd shapes by the incorporation of the elastic nylon mesh. The seamless, flexible impression is a negative mold which contains on its interior surfaces the finest details of the biological body member which in the case of a hand or part thereof faithfully reproduces every detail of the parts including fingernail, creases and skin texture.

The negative silicone mold is subsequently filled with melted wax whose excess is poured off after a layer 3 to 5 mm. in thickness solidifies on the interior surfaces of the mold. This results in a thin wax shell which is an exact model of the original biological body member. It should be noted that an important advantage of this invention is that the wax model has the desired posture of the parts, since positioning of the biological member which it duplicates was under direct observation while making of its impression by the painting of the RTV silicone onto it and correction of positioning of the parts performed as necessary before the silicone cured. This advantage is in contrast to the known prior "blind" methods wherein the biological body parts are submerged into a container of impression material which precludes direct observation or correcting of the positioning of the parts.

The modeling wax poured into the flexible negative impression mold is tinted to a blue color which will facilitate visualization of the fine surface details when the sculpturing of modifications is undertaken. Additionally, some of the wax of the same batch and therefore same color, is poured to form a thin sheet of wax which will be utilized in the subsequent scuplture and modifications of the model. After warming, any desired small corrections of curvatures of the thin wax shells are made. By sculpturing techniques that are known, the model is expanded, contracted or otherwise modified according to the dimension and specific requirements of the desired prosthetic device. In embodiments where the body being modeled corresponds to a hand or a finger, each fingernail position is provided with a sculptured wax protrusion which is substantially cylindrical and of maximum diameter permitted by the size of the fingernail. This extends outwardly for approximately a distance of one centimeter from the fingernail surface. Additionally, the cuticle and juncture of fingernail with the flesh surrounding the fingernail is sculptured to have a high degree of definition, essential to subsequent precision cutting away of the surface composed of the fingernail area. Areas of the model having deep cracks in the vicinity of the palm and skin creases of the fingers are partially filled-in to prevent the resulting prosthetic device from being excessively vulnerable to tear along these sharp lines.

In a known manner, the wax model is dusted with silver or otherwise subjected to some treatment which will render its surface electrically conductive. The wax model is then placed in an electroplating apparatus where a negative metal mold of precise details is deposited upon its surface. The wax is removed from the negative mold in a known manner. In accordance with the invention apertures are safely produced in the vicinity of the fingernail regions of the negative metal mold, or any other location selected for other devices than hands or fingers, by sawing off horizontally the hollow protrusions which project outward from the mold's surface. This highly advantageous aspect of the invention provides: (1) through and through ventilation of the molds for rapid and effective removal of solvents, and (2) a technique of achieving these precisely located apertures of maximum size without the hazzards associated with drilling holes through the molds. Experience has shown that drilling necessitated a very conservative size of the apertures since exact location cannot be known from the rough exterior surface of the negative molds on which details are ill-defined. Also, the new technique obviates possible damage to the delicate interior surface of the molds by spinning twisted metal ribbons about the bit. The concept of maximally large, safely produced and precisely placed apertures in the molds provides several distinct advantages described hereinbelow. When the mold needs to be closed to prevent escape of liquid dispersions, the resulting apertures are plugged temporarily with chemically inert material such as Teflon.

The negative metal mold is fitted with a removable cuff of relatively stiff paper which serves to extend temporarily the length of the mold and prevent foaming over of the liquid silicone dispersion during each subsequent degassing process. Otherwise, the mold must be excessively long in length and weight which complicates internal observations, handling and releasing of the glove after curing of the elastomer.

The negative mold with the plugged apertures is then filled with a liquid elastomer (for example, silicone) dispersion which will be used for forming the laminated outer most layer of the prosthetic device. In accordance with the invention, stable organic pigments are added to the liquid silicone providing a subtle tint adjusted to neutralize the gray hue characteristic of silicones. Thus, the liquid silicone remains translucent, but has a coloration similar to the epidermal layer of all normal human skin.

In accordance with the invention, the dispersion filled negative metal mold is placed in a high vacuum chamber so that degassing of the liquid occurs while the material is in the mold itself. This prevents the problem associated with known techniques with which liquid silicone or other elastomer dispersions are degassed in a separate container and subsequently poured into the mold. The latter known technique invariably results in the trapping of some air bubbles under the advancing lip of the poured material. Such air bubbles result in defects in the laminated layers of the prosthetic device rendering it imperfect.

After the degassing procedure, the first or outer layer of the silicone glove is produced on the detailed interior surface of the mold by pouring off excess silicone leaving a residual. The mold with the residual film of silicone on its surfaces is then installed on a double rotating machine which revolves in every plane simultaneously. Prior to rotation the plugs closing the apertures are removed to permit ventilation through the mold. In a practicable embodiment of the inventive method, double rotation is continued until there is sufficient evaporation of solvent from the silicone dispersion deposited on the mold's surfaces for it to become too viscous to flow or shift position on the mold surfaces. This method gives a distribution of bubble-free viscous silicone of equal thickness over all of the surfaces inside the mold.

A highly advantageous aspect of this invention is the introduction of a reliable system to utilize forced air ventilation to remove effectively solvents from the residual dispersion inside molds of the types discussed herein. After the solvent has evaporated to the point where the silicone residue is too viscous to flow, the mold in which ventilation ports have been created is attached to a high volume filtered air blower. The blower for molds similar in size to a human hand may have an air flow capacity of approximately 650 cubic feet per minute and provides efficient through and through forced air ventilation to facilitate further removal of the remaining solvent of the dispersion. Absolute removal of solvent is essential before the next coat of the silicone laminate is applied if defects are to be avoided and consistency of thickness is to be obtained.

The foregoing process of applying a degassed layer of liquid silicone dispersion to the interior of the mold is repeated with subsequent laminates until a desired thickness or number of such laminates is obtained.

In accordance with a highly advantageous aspect of the invention, the subsequent silicone dispesions are tinted with other stable organic pigments with the extent of such tinting being carefully adjusted so that the overall coloration of the laminated silicone layers collectively matches the lighest skin color of the body part of the patient for whom the device is being fabricated. Thus, for example, if a hand prosthesis is being made for a person of dark skin pigmentation, the coloration of the subsequent laminates is adjusted substantially to the light colored tissues of the palm region rather than the dark dorsal surfaces of the top of the hand.

The technique of using a high capacity blower in combination with the creation of openings at the distal most extremities of mold of the type discussed herein to permit through and through air flow ventilation provides an enormous reduction in the time required for fabrication of the outer portion of the prostheses as compared to prior methods. It also significantly improves the important consistency of thickness of the laminates. Production time is reduced to approximately 20% of that required by the known methods.

After removal of the last traces of solvent as described, the mold at room temperature is placed in an oven whose temperature is increased gradually to the level required for curing the particular elastomer according to specifications provided by the manufacturer of the particular material selected.

With the present invention release and extraction of the laminated silicone devices from the negative metal mold is greatly facilitated by being able to mechanically release distal parts by manipulations through the ventilation apertures. In a hand embodiment of the invention, each fingertip portion of the outer glove is teased loose from the mold surface and then pushed retrograde up into the palm of the glove with a smooth, blunt and malleable tool. This aspect of the invention not only has nearly eliminated tearing of gloves during extraction from the mold, but also has obviated the need for the application of chemical releasing agents to the molds surfaces, a step which significantly diminishes the precision of the details transferred from the mold. The wrist and palm portions of the glove are removed easily through the wide wrist opening by the application of steady traction and manipulation of the glove from the mold surface with a smooth instrument.

After removing the glove from the mold, final coloration is accomplished by working directly with the individual patient whose part being copied is positioned at a level corresponding to his heart level. As a major determinant of normal skin color of any part is its blood content, which varies widely with its position in relation to the heart, this technique stabilizes the color being duplicated. Pigmented silicones are applied to the deglazed interior surfaces of the cured and translucent, homogeneously-tinted silicone glove to match the individual characteristics of each patient. In one embodiment of the invention, RTV silicone is diluted with a volatile solvent into which is added stable organic pigments and blended on a palate to achieve the appropriate colors and tones required to match various areas. Without reversing the glove, as done with the known manner, the resulting opaque paint is applied to the interior of the glove, illustratively by an artist's brush while directly observing the result on the exterior surfaces which will be viewed by all subsequent observers. This achieves a remarkable life-like appearance and replication of individual characteristics not achievable by attempting color/detail matching from standard swatches or samples in the known manner.

The unique life-like appearance achieved from most patients, including blacks and others with deeply pigmented skin, by the methods of this invention, result from the concept of mimicking closely the natural pigmentation system of human skin. It results substantially in a clear outer layer corresponding to the epidermis of skin, moderately tinted middle layers corresponding to the superficial dermis, and the customized heavily pigmented final layers corresponding to the deep dermis and the vascular networks of the subdermal plexus. Collectively, the method of coloration of this invention described herein which so closely mimics the naturally occuring pattern of skin pigmentation is referred to as the BIO-CHROMATIC TM process.

The fingernail region of each finger, which also bears the ventilation apertures, is sharply defined by the deep sculpturing of the wax model previously described hereinabove. This region of the silicone glove is cut away to leave an opening which corresponds to the flesh out-line of a normal fingernail.

The fingernail which will be installed in the opening is fabricated to match the remaining fingernails of the individual patient. A clear acrylic outer shell is contoured to the shape of the fingernail in both transverse and longitudinal planes. On the underside thereof acrylics carefully adjusted in color to match the lunula, the sterile matrix, and the projecting distal fingernail are applied. The area of each follows precisely the size and shape and other details characteristic of the individual patient for whom the device is being fabricated. The central area of the colored acrylic representation of the sterile matrix is ground thin and filled with a white acrylic to simulate the normal capillary blanching of fingernail beds.

In accordance with the invention a coil of none corrosive material, such as stainless steel wire, is attached to the bottom of the fabricated fingernail. Such attachment is achieved with acrylics of the type used in the nail production and result in a secure fixation. At the back of the fingernail unit a shallow cut is made with a high speed burr to correspond to the curvature of the cuticle. This facilitates a sharp and clean juncture with the silicone glove and prosthetic fingernail in the cuticle area and a normal projection of the fingernail.

After the fingernail region of the glove has been cut away, the margins are tapered very thin with a rotating abrasive disc. The end of the glove finger is then filled with RTV silicone which has been tinted to match the basic skin color of the individual for whom the prostheses is being prepared. The prosthetic fingernail with its attached steel coil is then maneuvered into correct position with the coil being embedded in the silicone. Correct position is maintained during curing of the silicone into which the steel coil is embedded. Subsequently, the thin peripheral margins of the silicone are cemented to the acrylic fingernail with clear RTV silicone. The exposed surface of the fabricated fingernail is given a matte finish and final shaping is achieved with a conventional emory board.

After coloring of the glove and attachment of the fingernail is completed, the areas of the glove which are vulnerable to tearing, such as at skin creases, may be reinforced with dacron mesh fixed in place with skin-colored RTV silicone on the interior surface of the glove. The proximal end of the prosthesis is then trimmed to the best level to fit the individual patient.

The filling of the interior of the finished, thin and finely detailed exterior glove of the prosthesis is a critical and hitherto perplexing problem whose solution is an important component of this invention. If silicone foam or liquid dispersions are poured into a prosthetic glove as described herein, the solvents permeates and drastically distort permanently the shape of the whole prostheses. Circumventing this problem by preparing cured pieces of silicone in the shape of normal bones was one solution applied, but these must be individually placed inside the glove with only sufficient surface liquid silicone so that fixation is tedious, time consuming, inaccurate and frequently still results in gaps and distortion.

The solution incorporated in this invention lies substantially in prefabricating the internal filling units for prostheses. Work on this unit can be conveniently completed in the open and the unit cured before placement so that the solvent distortion problem is also eliminated. The technique embodied in this invention to obtain an internal unit of the exact shape but reduced in size by the thickness of the painted and finished exterior glove is to make a non-distortable shell of polyvinyl chloride (PVC) or other suitable material of 1.5 mm thickness in the same negative metal mold as used to produce the prosthetic glove to be filled. This shell serves as the mold for the internal filling unit. Any required modifications of shape of the filling unit or the incorporation of mechanical devices into it is readily achieved. Such devices or a positive model of the amputation stump on which the prosthesis is being fitted can be placed in the PVC mold before pouring into it material selected to form the filler unit to result in perfection of its subsequent fit to the patient. Firmness of the unit is adjustable depending upon the materials selected and the ratio of foam to solid elastomers chosen. Its color is adjusted by the addition of pigments to substantially the basic skin tone of the individual. After curing of the unit, it is removed from the PVC mold and fitted into the finished external prosthetic glove with a thin film of RTV elastomer tinted appropriately and applied to its surfaces. Simple, but secure, fixation of the versatile, perfectly-fitting, prefabricated internal filling unit is achieved in this manner. This most important aspect of the invention has not only eliminated the problems of glove distortion, poor fitting and damage to previously completed steps, but has drastically reduced the long and tedious periods of time required for this to relief of both technicians and patients.

After final placement and fixation of the prefabricated interior filling unit and confirming a satisfactory fit on the patient, the exterior surface is cleaned and polished. The exposed interior of the prostheses is then smoothly finished with a thin film of flesh-tinted silicone flowed over the surfaces for comfort and to facilitate cleaning of the device.

BRIEF DESCRIPTION OF THE DRAWINGS

Comprehension of the invention is facilitated by reading the following further description in conjunction with annexed drawings, in which:

FIGS. 1A–1C are isometric representations of a wax model of a finger embodiment of the invention showing a wax-sculptured substantially cylindrical protrusion.

FIGS. 1A–1C are isometric representations of a wax model 10A, 10B and 10C of a human finger having a fingernail region 12 which has been defined by a sharp sculptured ridge 13.

In accordance with the invention, fingernail region 12 is provided with a substantially cylindrical protrusion 15 which is formed of wax, as is wax finger 10A, and located precisely on the fingernail region in the case of a hand but the same principle can be equally applied to molds of other parts. Thus, after wax finger 10A is metallized, as described hereinabove, a corresponding protrusion will form on the fingernail region 10B which is substantially sawed off to form the precisely placed, maximum caliber ventilation ports, (See 10C) without danger of damage to the delicate interior surfaces of the mold. As indicated hereinabove, the ventilation ports serve the dual function of permitting through and through ventilation effectively enhancing the removal of solvent from the silicone dispersion, and also to facilitate removal of the cured glove usually without releasing agents after the negative metal mold with the elastomer deposited on its interior surfaces (not shown) is removed from the curing oven.

Figure 2A:
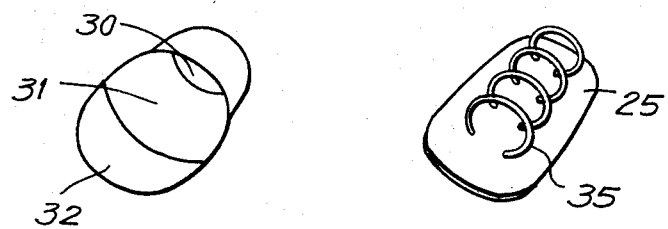
FIGS. 2A–2C are isometric representations of a fingertip showing the manner in which a prosthetic fingernail is secured thereto using a wire coil.
Figure 2B:
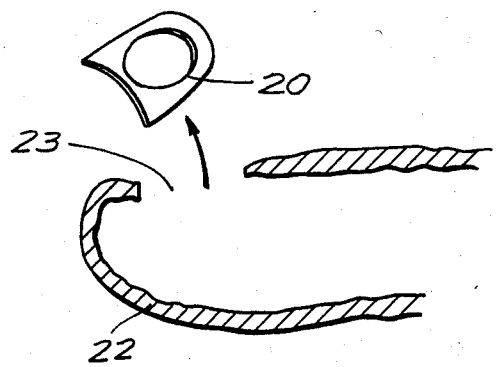
Figure 2C:
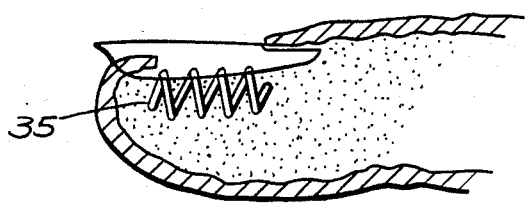

FIGS. 2A–2C are isometric representations of a fingertip 20 of a silicone glove 22 constructed in accordance with the invention. As discussed above with respect to FIGS. 1A–1C, sharply sculptured ridge 13 surrounds the fingernail region and provides a guide for the removal of the fingernail region of fingertip 20 by means of a sharp instrument, such as a surgical knife. Once the fingernail region has been removed, an opening 23 results in the fingertip. As described hereinabove, through opening 23 the end of the silicone finger is filled with RTV silicone which has been colored to match the basic skin tones of the patient. A prosthetic fingernail assembly 25 is formed of colored acrylics corresponding to a lunula 30, a sterile matrix 31, and a protruding distal fingernail 32. As previously indicated, the coloring of the fingernail is selected to match the remaining fingernails of the patient. A step is cut at the cuticle line to facilitate a perfect in-laid juncture with the prosthetic glove.

A stainless steel wire coil 35 is affixed to underside of fingernail assembly 25 by an acrylic composition. Fingernail assembly 25 is then placed over opening 23 in fingertip 20 and maneuvered into proper position as its stainless steel coil 35 is embedded in the RTV silicone filling the fingertip. The fingernail assembly is held in place until the silicone is cured which securely affixes it to the fingertip. Subsequently, the peripheral portion of opening 23, whose margins have been ground thin, as described hereinabove, are cemented to the fingernail assembly.

Although the invention has been described in terms of specific embodiments and applications, persons skilled in the art, in light of this teaching, can generate additional embodiments without exceeding the scope or departing from the spirit of the claimed invention. Accordingly, it is too be understood that the drawings and descriptions in this disclosure are proffered to facilitate comprehension of the invention and should not be construed to limit the scope thereof.

What is claimed is:

1. A method of making a prosthetic device for wearing on a normally visible anatomical appendage of the human body, said device being strong, flexible, seamless, non-irritating and aesthetically life-like in appearance, which method comprises the steps of:
   (1) forming a first flexible impression mold by applying a coating of a curable, liquid elastomer material onto a biological body member of which the prosthetic device is to be a duplicate, while monitoring and correction of positioning, as necessary, to assure that the biological member is in its most natural appearing state;
   (2) removing said first flexible impression mold after curing said elastomeric material at least sufficiently to effect removal of said mold without tearing;
   (3) contacting the interior surface of said impression mold with a wax-like material in liquid form and which upon solidification and removal of the flexible impression mold, provides a duplicate and finely detailed model of said biological member which can be further positioned and scupltured, if desired;
   (4) providing one or more pluggable ventilation apertures on said model;
   (5) rendering the surface of said model electrically conductive;
   (6) electrodepositing metal onto the surface of said model;
   (7) removing said wax-like model to provide a metal negative mold of said body member;
   (8) contacting the inner surface of said metal mold with a curable, liquid elastomeric material to form the outermost layer of said prosthetic device;
   (9) subjecting said metal mold to rotational conditions to evenly disperse said material within said mold;
   (10) repeating steps (8) through (9) until a multi-layer thickness is obtained sufficient for said prosthetic device,
   (11) curing said elastomeric material and thereafter removing the prosthetic device from said mold; and
   (12) adding pigments and coloring materials to at least some of said layers in said prosthetic devices to mimic natural skin pigmentation and coloration.

2. The method of claim 1, wherein said forming step further includes the steps of applying a first thin coating of said curable liquid elastomeric material to said biological body member, covering at least a portion of the coated body member with a strong, flexible mesh member and applying a second coating of said curable liquid elastomeric material onto said body member, whereby said first flexible impression mold can be removed from irregularly shaped parts, such as a hand, without tearing.

3. The method of claim 1, wherein there is further included the steps of temporarily extending the length of said metal mold with a removable cuff of relatively stiff material to prevent foaming over of said liquid elastomeric material during a subsequent degassing process and thereafter subjecting said elastomeric material within said metal mold to vacuum conditions to degass said elastomeric material while still in the mold.

4. The method of claim 1, wherein there is further included the step of subjecting said metal mold to solvent removal conditions utilizing said ventilation apertures by unplugging said pluggable ventilation apertures while said metal mold is being rotated and thereafter by further applying high-volume filtered air to said ventilation apertures.

5. The method of claim 1, wherein said step of providing one or more pluggable ventilation apertures includes the step of precisely placing a wax cylinder perpendicular to the surface of a fingernail portion of said wax-like model, said cylinders being of sufficient diameter to extend almost the full width of said fingernail portion and, subsequent to electrodeposition of metal onto the surface of said cylinders, removing said cylinders to provide openings to the interior of said metal mold.

6. The method of claim 1, wherein said step of adding pigments and coloring materials includes the steps of adjusting the hue of an outer layer of said prosthetic device, such that it remains clear, coloring a middle layer so that it homogeneously matches the tone of the lighest colored area of skin being matched and applying elastomer paints to interior layers according to skin color variations of the individual being fitted with the prosthetic device.

7. The method of claim 1, wherein there is further included the steps of cutting away a fingernail region of said prosthetic device in the area of said ventilation apertures, filling the interior of said prosthetic device in the area of said fingernail region with RTV silicone tinted to match a basic skin color, embedding a non-corrosive wire coil in said RTV silicone, to which is attached a prosthetic fingernail and curing said RTV silicone to permanently affix said fingernail to said prosthetic device.

8. The method of claim 1, wherein there is further provided the step of prefabricating a precisely dimensioned internal filling unit for said prosthetic device, said prefabricated unit being an exact replicate of an external glove-like portion of the prosthetic device, but reduced in dimension by the thickness of the layers of the glove-like portion of the prosthetic device, said prefabricated unit being subsequently inserted into the glove-like portion of the prosthetic device.

9. A method of making a prosthetic hand device for the human body, said device being strong, flexible, seamless, non-irritating and aesthetically life-like in appearance, which method comprises the steps of:
   (1) forming a first flexible impression mold by:
      (a) applying a first thin coating of a curable liquid elastomeric material onto a human hand of which the prosthetic device is to be a duplicate;
      (b) covering at least a portion of the coated hand with a strong flexible mesh member;
      (c) applying a second coating of said curable liquid elastomeric material onto said hand;

(d) monitoring and correction of positioning, as necessary, to assure that the hand is in its most natural appearing state;

(2) removing said flexible impression mold after curing said elastomeric material at least sufficiently to effect removal of said mold without tearing;

(3) contacting the interior surface of said depression mold with a wax-like material in liquid form, in which upon solidification and removal of the flexible impression mold, provides a duplicate and finely detailed model of said hand, which can be further positioned and sculptured if desired;

(4) providing one or more ventilation apertures on at least some of the fingernails of said model;

(5) rendering the surface of said model electrically conductive;

(6) electro-depositing metal onto the surface of said model;

(7) removing said wax-like models to provide a metal negative mold of said hand;

(8) removing a portion of said ventilation aperture to provide free access to the interior of said mold and contacting the inner surface of said mold with a curable liquid elastomeric material to form the outer most layer of said prosthetic device;

(9) subjecting said elastomeric material within said metal mold to vacuum conditions to degass said elastomeric material;

(10) subjecting said metal mold to rotational conditions to evenly disburse said material within said mold;

(11) subjecting said mold to solvent removal conditions utilizing said ventilation apertures;

(12) repeating steps (8) through (11) until a multilayer thickness is obtained sufficient for said device and wherein pigments in coloring materials are added to at least some of said layers to mimic natural skin pigmentation and coloration;

(13) curing said elastomer material;

(14) removing said prosthetic hand device from said mold; and

(15) covering said ventilation apertures by afixing to said prosthetic hand device synthetic fingernail members.

10. The method of claim 9, wherein said elastomeric material is room temperature vulcanizable silicone.

11. The method of claim 9, wherein said mesh is comprised of nylon.

12. The method of claim 9, wherein said ventilation apertures on said model are wax cylinders disposed perpendicular to the surface of the fingernail portion of said hand.

13. The method of claim 12, wherein said cylinders are of sufficient diameter to extend almost to the width of said fingernails.

14. The method of claim 12, wherein after electrodeposition of metal onto the surface of said model, the cylinders are removed to provide openings to the interior of said metal mold on the surface of the fingernails.

15. The method of claim 14, wherein said ventilation apertures are temporarily plugged.

16. A method of making a prosthetic finger device for the human body, said device being strong, flexible, seamless, nonirritating and aesthetically life-like in appearance, which method comprises the steps of:

(1) forming a first flexible impression mold by:
   (a) applying coating of a curable liquid elastomeric material onto a human finger of which the prosthetic device is to be a duplicate;
   (b) monitoring and correction of positioning, as necessary, to assure that the finger is in its most natural appearing state;

(2) removing said flexible impression mold after curing said elastomeric material at least sufficiently to effect removal of said mold without tearing;

(3) contacting the interior surface of said depression mold with a wax-like material in liquid form, in which upon solidification and removal of the flexible impression mold, provides a duplicate and finely detailed model of said finger, which can be further positioned and sculputured if desired;

(4) providing one or more ventilation apertures on at least some of the fingernails of said model;

(5) rendering the surface of said model electrically conductive;

(6) electrodepositing metal onto the surface of said model;

(7) removing said wax-like models to provide a metal negative mold of said finger;

(8) removing a portion of said ventilation aperture to provide free access to the interior of said mold and contacting the inner surface of said mold with a curable liquid elastomeric material to form the outer most layer of said prosthetic device;

(9) subjecting said metal mold to vacuum conditions to degass said elastomeric material;

(10) subjecting said metal mold to rotational conditions to evenly disburse said material within said mold;

(11) subjecting said mold to solvent removal conditions utilizing said ventilation apertures;

(12) repeating steps (8) through (11) until a multilayer thickness is obtained sufficient for said device and wherein pigments in coloring materials are added to at least some of said layers to mimic natural skin pigmentation and coloration;

(13) curing said elastomer material;

(14) removing said prosthetic hand device from said mold; and

(15) covering said ventilation apertures by afixing to said prosthetic finger device synthetic fingernail members.

17. The method of claim 16, wherein said elastomeric material is room temperature vulcanizable silicone.

18. The method of claim 16, wherein said mesh is comprised of nylon.

19. The method of claim 18, wherein said ventilation apertures on said model are wax cylinders disposed perpendicular to the surface of the fingernail portion of said hand.

20. The method of claim 19, wherein said cylinders are of sufficient diameter to extend almost to the width of said fingernails.

21. The method of claim 19, wherein after electrodeposition of metal onto the surface of said model, the cylinders are removed to provide openings to the interior of said metal mold on the surface of fingernails.

22. The method of claim 21, wherein said ventilation apertures are temporarily plugged.

* * * * *